US00PP13755P39

(12) United States Plant Patent
Scheffers

(10) Patent No.: US PP13,755 P3
(45) Date of Patent: Apr. 29, 2003

(54) DRACAENA PLANT NAMED '0104SJ'

(76) Inventor: Ruud A. M. Scheffers, Plaats 9, 2675 CK, Honselersdijk (NL)

( * ) Notice: Subject to any disclaimer, the term of this patent is extended or adjusted under 35 U.S.C. 154(b) by 0 days.

(21) Appl. No.: 09/962,206

(22) Filed: Sep. 26, 2001

(65) Prior Publication Data

US 2002/0120970 P1 Aug. 29, 2002

(30) Foreign Application Priority Data

Feb. 26, 2001 (EP) ..... 2001/0358

(51) Int. Cl.[7] ..... A01H 5/00

(52) U.S. Cl. ..... Plt./383

(58) Field of Search ..... Plt./383

*Primary Examiner*—Bruce R. Campell
*Assistant Examiner*—Susan B. McCormick
(74) *Attorney, Agent, or Firm*—Foley & Lardner

(57) ABSTRACT

A distinct Dracaena plant named '0104SJ' characterized by its compact growth habit, growth rate 10–20% higher than Dracaena 'White Jewel'; narrow, ensiform leaves; leaf length of 30 cm and leaf width of 6.5 cm; leaf coloration: dark green margin, closest to RHS 139A; pure white stripes next to margin; center color is light grey green, RHS 190D; stripes along center are green, RHS 139A and greyish green, RHS 189D, with whiteish stripes.

2 Drawing Sheets

LATIN NAME OF THE GENUS AND SPECIES OF THE PLANT CLAIMED

*Dracaena Vand.* Ex. *L. fragrans* (group Compacta)

VARIETY DENOMINATION

'0104SJ'

BACKGROUND OF THE INVENTION

The present invention comprises a new and distinct cultivar of Dracaena plant botanically known as *Dracaena Vand.* Ex. *L. fragrans* (group Compacta) and hereinafter referred to by the cultivar name '0104SJ'.

The new cultivar was selected by the inventor, Ruud A. M. Scheffers, in Honselersdijk, The Netherlands, in July 1998. The new cultivar was obtained as a natural mutation of *Dracaena Vand.* Ex *L. fragrans* (group Compacta) 'White Jewel' (U.S. Plant Pat. No. 12,433).

The new cultivar was first asexually propagated by the inventor in Honselersdijk, The Netherlands, in October 1998. Subsequent asexual reproduction of the new cultivar by division has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and in combination distinguish '0104SJ' as a new and distinct cultivar:

1. compact growth habit;

2. growth rate 10–20% higher than Dracaena 'White Jewel';

3. narrow, ensiform leaves;

4. leaf length of 30 cm and leaf width of 6.5 cm;

5. leaf coloration: dark green margin, closest to RHS 139A; pure white stripes next to margin; center color is light grey green, RHS 190D; stripes along center are green, RHS 139A and greyish green, RHS 189D, with whiteish stripes.

'0104SJ' has not been observed under all possible environmental conditions. The phenotype on the new cultivar may vary significantly with variations in environment such as temperature, light intensity, and daylength without any change in genotype. The following observations, measurements and values describe plants grown in Honselersdijk, The Netherlands under greenhouse conditions which closely approximate those generally used in horticultural practice.

In comparison with the well-known Dracaena cultivar *Dracaena Vand.* Ex. *L. fragrans* (group Compacta) 'Ulises' (unpatented), '0104SJ' grows much more compact, the leaves of '0104SJ' are shorter and stronger than the leaves of 'Ulises'. In comparison to 'White Jewel' (U.S. Plant patent application Ser. No. 09/326,615) '0104SJ' has relatively more green in the leaves than 'White Jewel', and '0104SJ' also has shorter and stronger leaves.

BRIEF DESCRIPTION OF THE DRAWINGS

The first drawing illustrates a 16-weeks old plant of Dracaena '0104SJ' propagated from a top, with colors being as true as possible with illustrations of this type. The second drawing illustrates a 16-weeks old plant of Dracaena '0104SJ' propagated from a top and a 16-week old plant of Dracaena 'White Jewel', with colors being as true as possible with illustrations of this type.

DETAILED BOTANICAL DESCRIPTION

Color references are made to The Royal Horticultural Society Colour Chart (R.H.S.), except where general colors of ordinary significance are used. Colors are approximate as color depends on horticultural practices such as light level and fertilization rate, among others.

Parentage: *Dracaena Vand.* Ex. *L. fragrans* (group Compacta) 'White Jewel'.

Propagation: Primarily by vegetative division of the plant head or apical meristem.

General observations:

*Growing conditions.*—'0104SJ' is grown in a greenhouse. The grower propagates '0104SJ' in a normal commercial greenhouse under temperatures of 20–21 degrees Celsius day and night. As with most Dracaena varieties, '0104SJ' does not stand direct sunlight, so sun shields are closed when sunlight becomes to bright. No artificial lighting or photoperiodic treatments are conducted. Highest temperature resistance is at least 40 degrees Celsius, lowest is 5 degrees Celsius. Resistance, tolerance and susceptibility to stresses, pathogens and pests is very good. Compound fertilizer is added to the soil. There are no other cultural or environmental treatments.

Plant habit:

*Growth rate.*—10–20% higher than Dracaena 'White Jewel'.

*Form.*—Medium compact, slightly elongated.

*Plant height.*—Approximately 30 cm.

*Plant width.*—Approximately 65 cm.

Leaves:

*Form and size.*—Narrow, ensiform with parallel ribs in the length: approximately 30 cm in length and 6.5 cm in width, base is cuneate, tip is accuminate.

*Leaf arrangement.*—Spiral.

*Texture.*—Strong and leathery.

*Veins.*—One main vein, visible only on the underside of the leaf (mid-rib), RHS 139 C.

*Upper side color.*—Margin is darker green but closest to RHS 139 A and approximately 2 cm in width. The width of (all color) stripes differs per leaf, the very center is light grey green RHS 190 D, the stripe next to the margin is pure white (no R.H.S. comparable color), the approximately 1.4 cm wide stripes on both sides of the very center stripe is a composition of various colors and sizes, thinner lines of green (including RHS 139 A), greyish green (including RHS 189 D) and almost white lines up.

*Under side Color.*—Similar to the upper side only lighter. Distinct difference is the mid-rib which is thick and green (RHS 139C) and at the base approximately 6 mm wide.

*Margin.*—Entire and slightly curled.

*Depth.*—Medium.

*Number.*—Approximately 21 to 25 per 16-week old plant propagated from a top.

Flowers: No flowers observed to date.

Stem:

*Length.*—Short, approximately 3 cm.

*Diameter.*—2 cm and formed by bases of leaves.

*Color.*—green (RHS 145 C) to white.

*Other.*—Strong.

*Roots.*—Orange-brown (RHS 168 D) in color, it takes approximately 3 weeks to initiate roots and approximately 7 weeks are needed to produce a rooted liner.

Plant disease/insect tolerance: '0104SJ' has a very high resistance against diseases and a very high tolerance against insects.

Reproductive organs: No flowers observed to date.

I claim:

1. A new and distinct cultivar of Dracaena plant named '0104SJ', as described and illustrated herein.

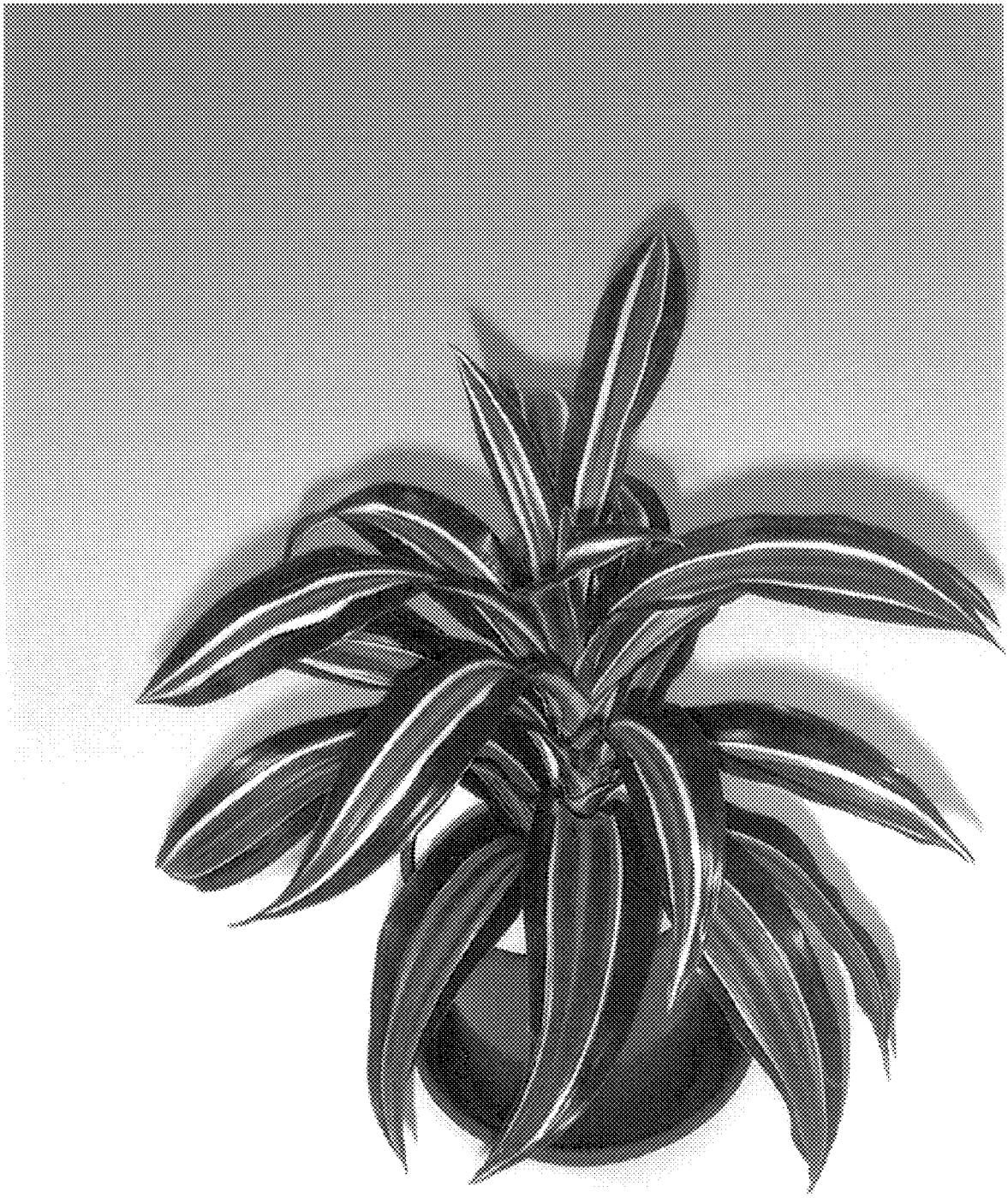

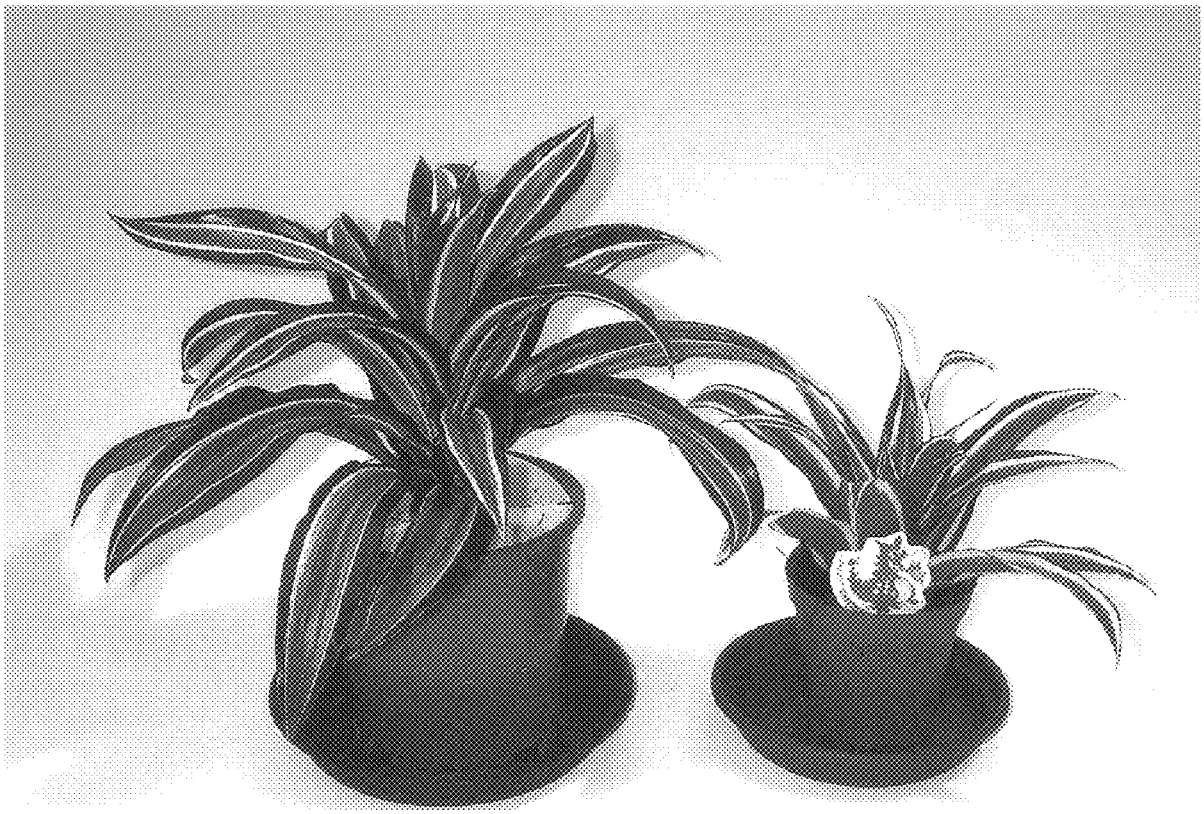

* * * * *